(12) United States Patent
Meng et al.

(10) Patent No.: US 8,518,481 B2
(45) Date of Patent: Aug. 27, 2013

(54) INTERCONNECT FOR MEMS DEVICE INCLUDING A VISCOELASTIC SEPTUM

(75) Inventors: Ellis Meng, Pasadena, CA (US); Ronalee Lo, Monterey Park, CA (US)

(73) Assignee: University of Southern California

( * ) Notice: Subject to any disclaimer, the term of this patent is extended or adjusted under 35 U.S.C. 154(b) by 0 days.

(21) Appl. No.: 13/251,959

(22) Filed: Oct. 3, 2011

(65) Prior Publication Data
US 2012/0017423 A1  Jan. 26, 2012

Related U.S. Application Data

(62) Division of application No. 12/357,330, filed on Jan. 21, 2009, now Pat. No. 8,087,310.

(60) Provisional application No. 61/011,462, filed on Jan. 17, 2008.

(51) Int. Cl.
*B05D 7/00* (2006.01)

(52) U.S. Cl.
USPC ........................ 427/240; 427/255.6; 427/256

(58) Field of Classification Search
USPC ...................................... 427/240, 255.6, 256
See application file for complete search history.

(56) References Cited

U.S. PATENT DOCUMENTS

| | | | |
|---|---|---|---|
| 6,106,900 A | 8/2000 | Innes et al. | |
| 6,360,779 B1 | 3/2002 | Wagner et al. | |
| 6,956,283 B1 * | 10/2005 | Peterson | 257/680 |
| 7,435,952 B2 * | 10/2008 | Finlay et al. | 250/292 |
| 2003/0146216 A1 | 8/2003 | Torres-White et al. | |
| 2006/0223164 A1 | 10/2006 | Orwar et al. | |
| 2007/0072287 A1 | 3/2007 | Morisette et al. | |
| 2010/0080733 A1 | 4/2010 | Carlson et al. | |

* cited by examiner

*Primary Examiner* — Kirsten Jolley
(74) *Attorney, Agent, or Firm* — Stetina Brunda Garred & Brucker

(57) ABSTRACT

Provided is a micro electro mechanical systems (MEMS) device for use with an elongate structure. The MEMS device includes a generally planar substrate, a device wall layer formed upon the substrate, a septum cavity formed in the device wall layer, a channel formed in the device wall layer in fluid communication with the septum cavity, and a septum element disposed in the septum cavity. The septum element is formed of a viscoelastic material. The septum element defines a septum entry surface and a septum exit surface with the septum exit surface being exposed to the channel and disposed between the septum entry surface and the channel. The septum element is without any openings formed through the septum element extending between the septum entry and exit surfaces. Methods of manufacturing and interacting with the MEMS device are also provided.

4 Claims, 4 Drawing Sheets

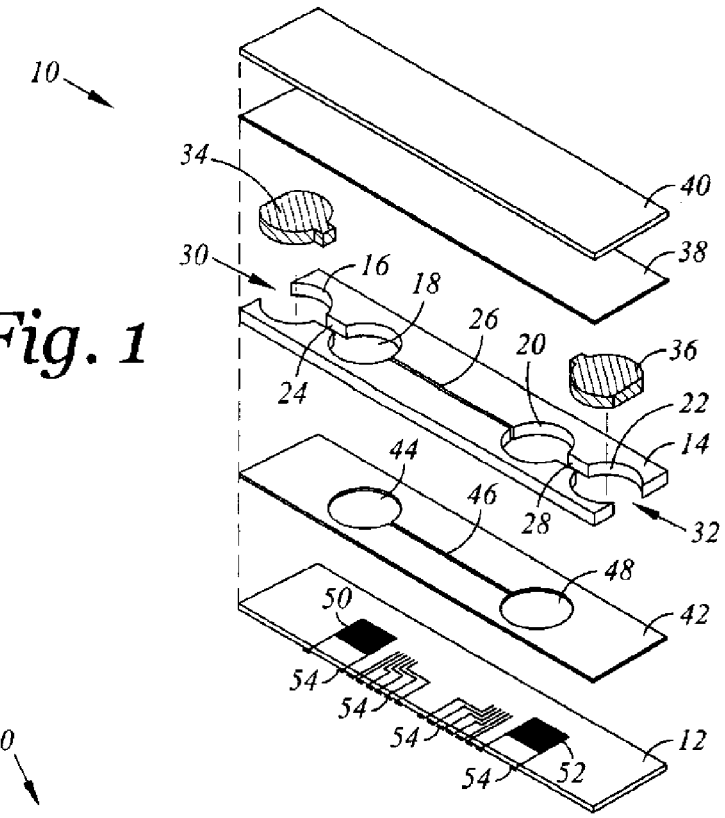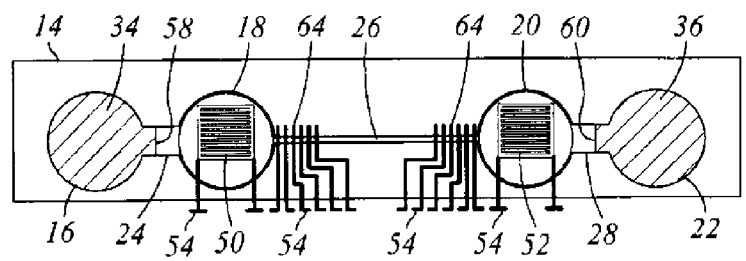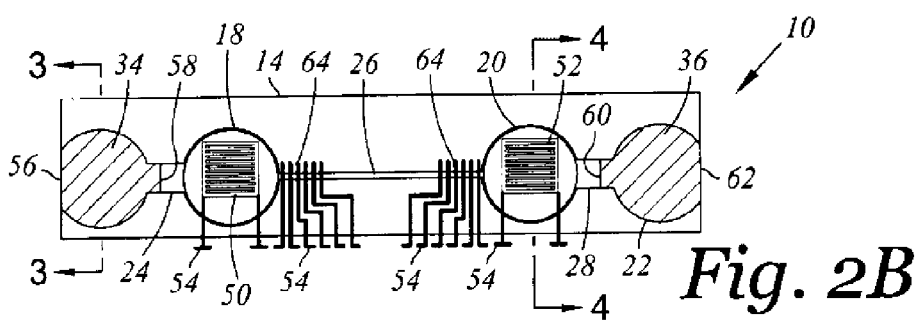

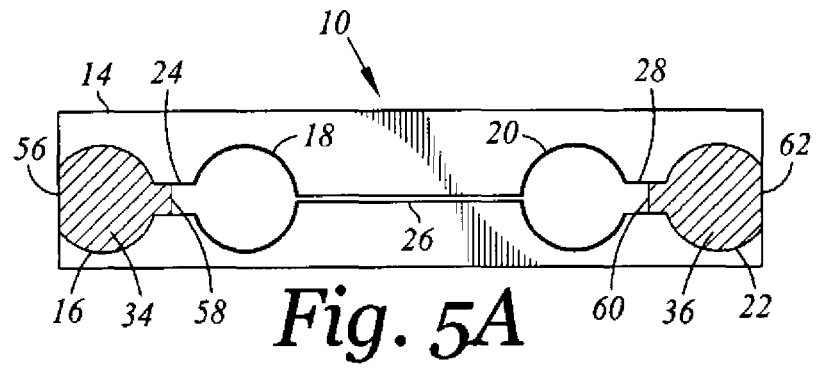
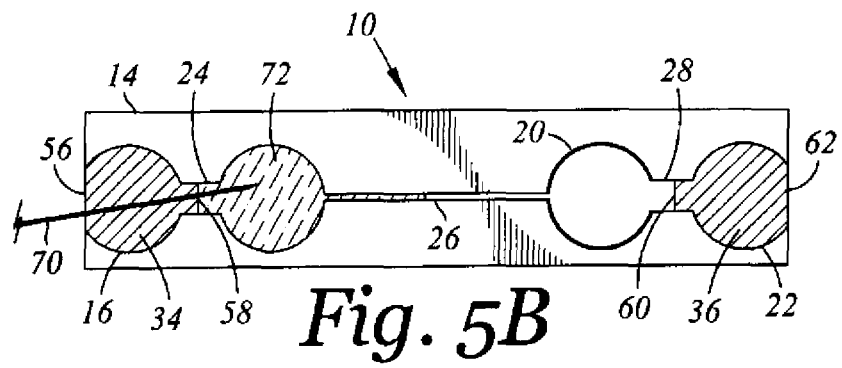
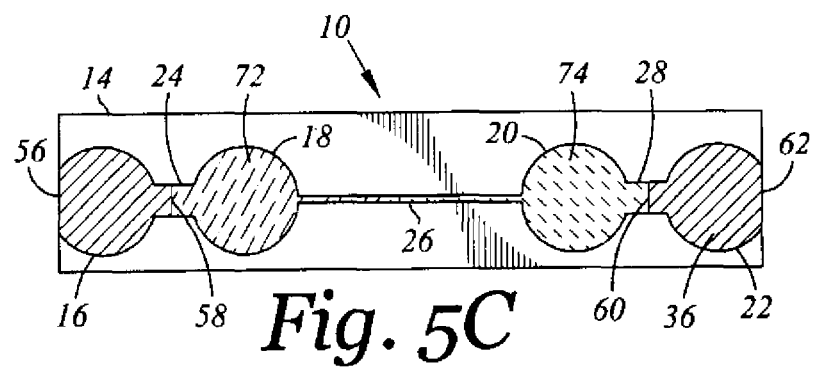
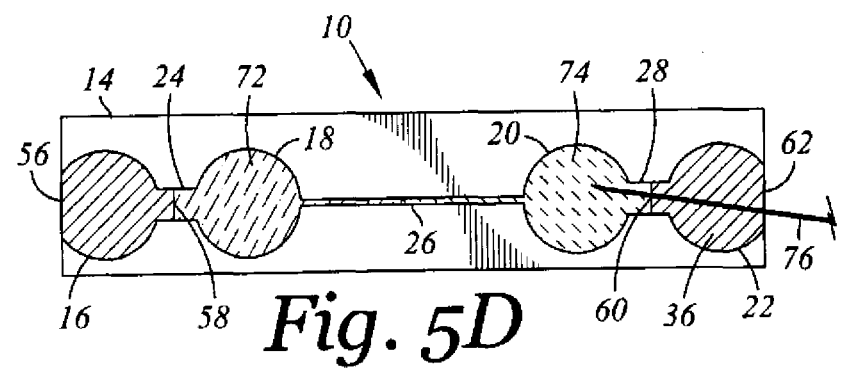

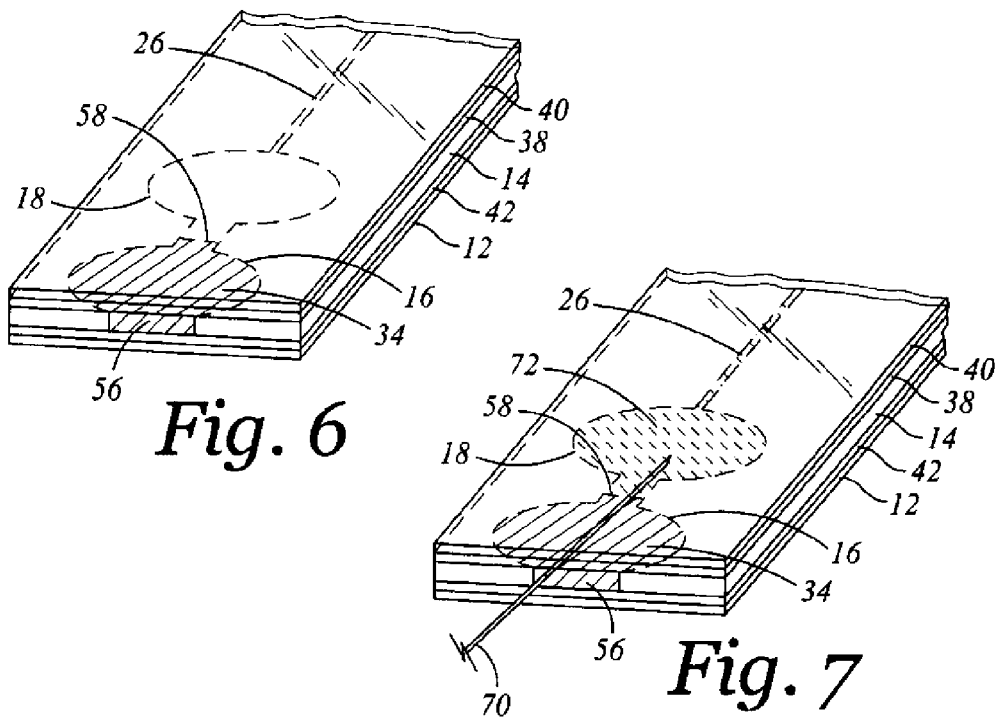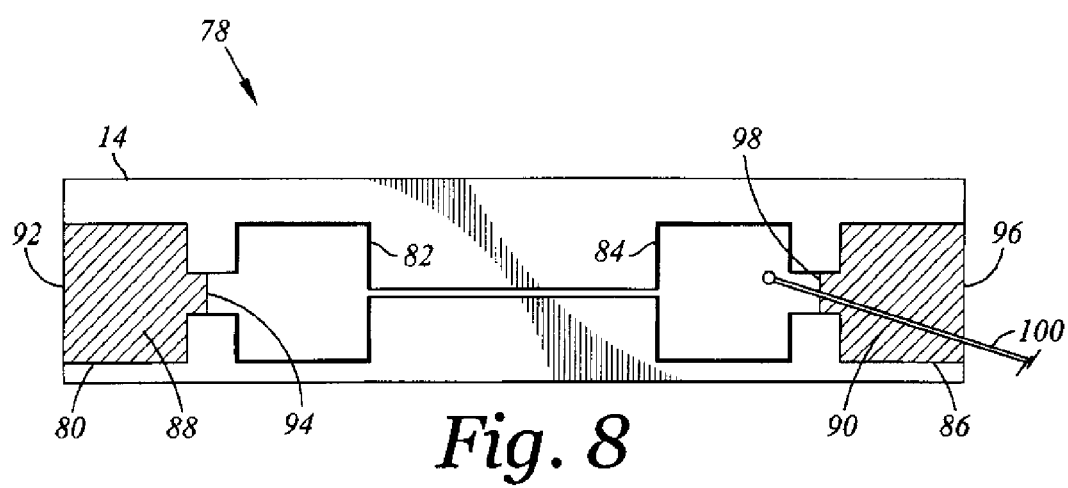

INTERCONNECT FOR MEMS DEVICE INCLUDING A VISCOELASTIC SEPTUM

CROSS-REFERENCE TO RELATED APPLICATIONS

This application is a divisional patent application of and claims the benefit of the earlier filing date of U.S. patent application Ser. No. 12/357,330 (filed on Jan. 21, 2009 now U. S. Pat. No. 8,087,310, the entire contents of which are incorporated herein by reference). This application is also related to and claims the benefit of the earlier filing date of U.S. Provisional Patent Application No. 61/011,462, entitled INTERCONNECT FOR MEMS DEVICE INCLUDING A VISCOELASTIC SEPTUM, filed on Jan. 17, 2008, the entire contents of which are incorporated herein by reference. It is noted that Monday, Jan. 19, 2009, and Tuesday, Jan. 20, 2009, are each a "Federal holiday within the District of Columbia" (See MPEP 710.05 and TEMP 308).

STATEMENT RE: FEDERALLY SPONSORED RESEARCH/DEVELOPMENT

Grant No. EEC-0310723 (USC AC. NO. 5345087106) from the National Science Foundation (NSF); and Grant No. EEC-0547544 (USC AC. NO. 5345083420) from the National Science Foundation (NSF).

BACKGROUND OF THE INVENTION

1. Field of the Invention

The present invention relates generally to micro electro mechanical systems (MEMS) devices, and more particularly to an interconnect for a MEMS device including a viscoelastic septum.

2. Description of the Related Art

In the context of micro electro mechanical systems (MEMS) devices, macro-to-micro fluidic connections and packaging is an on-going challenge despite many efforts. In the macro world, connections are easily achieved due to the wealth of commercially available plumbing options. Standard prefabricated tubing and fittings are easily configured to achieve the desired result. Presently, MEMS devices have yet to be massively utilized in the commercial context and thus far have been utilized in the research and development stages. The micro-fluidics world, which involves dimensions on the order of millimeters or smaller, does not have a readily available supply of fluidic connection products.

The complexity of simultaneously managing the need for precision alignment, adhesives, and/or extra fabrication steps has limited the use of existing methodologies which are primarily focused on out-of-plane connection formats. In an out-of-plane connection format, a fitting or tubing may be attached to a MEMS device to provide an interconnect. However, a trade-off commonly encountered in these out-of-plane interconnects is the dramatic increase in dead volume and space to accommodate the spatial separation between connections necessary to avoid microscope objectives during viewing.

Some prior art solutions to provide fluidic connections to micro flow channels is to manually align and glue tubing to ports. Needless to say, this method is only practical for making a few one-time connections to prototypes. Batch processing and mass fabrication cannot rely on such an unreliable and time consuming method. Other drawbacks include complex assembly, misalignment, large footprint, and permanence of the connection. Even for the purposes of research, the numerous disadvantages of this method can outweigh its usefulness.

As is apparent from the foregoing, there exists a need in the art for an improved interconnect for MEMS devices in comparison to the prior art.

BRIEF SUMMARY OF THE INVENTION

According to an aspect of the present invention, there is provided a micro electro mechanical systems (MEMS) device for use with an elongate structure. The MEMS device includes a generally planar substrate, a device wall layer formed upon the substrate, a septum cavity formed in the device wall layer, a channel formed in the device wall layer in fluid communication with the septum cavity, and a septum element disposed in the septum cavity. The septum element is formed of a viscoelastic material. The septum element defines a septum entry surface and a septum exit surface with the septum exit surface being exposed to the channel and disposed between the septum entry surface and the channel. The septum element is without any openings formed through the septum element extending between the septum entry and exit surfaces.

In further detail, the device wall layer may be formed of a polymer material, such as an epoxy resin. The device wall layer may be formed of a rigid material. The septum element may be formed of a silicon material. The septum element may be formed of a polydimethylsiloxane (PDMS). The septum element may define a fluid-tight seal with the device wall layer at the septum cavity with respect to fluid leakage between the channel and the MEMS device adjacent the septum entry surface. The elongate structure may define a longitudinal length and a structure cross-sectional area orthogonal to the longitudinal length. The septum element extends a distance between the septum entry and exit surfaces parallel to the substrate less than the longitudinal length, and the septum element extends across an area orthogonal to the substrate greater than the structure cross-sectional area.

In accordance with another embodiment of the invention, there is provided a method of manufacturing a micro electro mechanical systems (MEMS) device for use with an elongate structure. The method includes the steps of forming a generally planar substrate, forming a device wall layer upon the substrate, forming a septum cavity in the device wall layer, forming a channel formed in the device wall layer in fluid communication with the septum cavity, and forming a septum element disposed in the septum cavity. The septum element is formed of a viscoelastic material. The septum element defines a septum entry surface and a septum exit surface with the septum exit surface being exposed to the channel and disposed between the septum entry surface and the channel and the septum element being without any openings formed through the septum element extending between the septum entry and exit surfaces.

In further detail, the method may include depositing parylene upon the substrate. The method may include spin coating an epoxy resin upon the parylene. The method may include curing the epoxy resin into a solid material. The method may include pouring a polymer in the septum cavity and curing the polymer to form the septum element.

According to another embodiment of the present invention, there is provided a method of interacting with a micro electro mechanical systems (MEMS) device. The method includes providing a MEMS device. The MEMS device includes a generally planar substrate, a device wall layer formed upon the substrate, a septum cavity formed in the device wall layer, a channel formed in the device wall layer in fluid communication with the septum cavity, a septum element disposed in the septum cavity. The septum element formed of a viscoelastic material. The septum element defines a septum entry surface and a septum exit surface with the septum exit surface being exposed to the channel and disposed between the septum entry surface and the channel and the septum element being without any openings formed through the septum element extending between the septum entry and exit surfaces. The method further includes piercing the septum entry surface with an elongate structure, and extending the elongate structure through the septum exit surface into the channel. The elongate structure may form a pierced opening through the septum element, and the method further includes removing the elongate structure from the septum element through the pierced opening. The method may further include maintaining a fluid-tight seal of the pierced opening after removal of the elongate structure. The elongate structure may be a needle, and the method may further include injecting a fluid into the channel through the needle. The elongate structure may be a sensor, and the method may include sensing a physical characteristic of the channel using the sensor.

BRIEF DESCRIPTION OF THE DRAWINGS

These and other features and advantages of the various embodiments disclosed herein will be better understood with respect to the following description and drawings in which like numbers refer to like parts throughout and in which:

FIG. 1 is an exploded perspective view of a micro electro mechanical systems (MEMS) device that includes septum elements in accordance with an aspect of the present invention;

FIG. 2A is a top plan view of a MEMS device in accordance with an aspect of the present invention, as seen in a prior fabrication step (not all layers are depicted for ease of illustration);

FIG. 2B is a top plan view of the MEMS device of FIG. 2A as finally fabricated (not all layers are depicted for ease of illustration);

FIG. 5A is a top plan view of the MEMS device of FIG. 2B (without some features depicted for ease of illustration);

FIG. 5B is top plan view of the MEMS device of FIG. 5A as shown with a first needle inserted through a first septum element and having injected a working fluid into the MEMS device;

FIG. 5C is top plan view of the MEMS device of FIG. 5B with a working gas having been created in the MEMS device;

FIG. 5D is top plan view of the MEMS device of FIG. 5C as shown with a second needle inserted through a second septum element for removing the working gas from the MEMS device;

FIG. 6 is a top end perspective view of a portion the MEMS device of FIG. 5a with the first septum;

FIG. 7 is a top end perspective view of a portion the MEMS device of FIG. 5b with the first needle; and FIG. 8 is a top plan view of a MEMS device according to another embodiment with first and second septum elements in a square configuration and a sensor.

DETAILED DESCRIPTION OF THE INVENTION

Figure 3A:
FIGS. 3A-H are cross sectional views of a MEMS device as depicted along an axis 3-3 of FIG. 2B illustrating various states of fabrication.
Figure 3B:
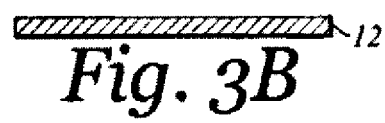

The detailed description set forth below in connection with the appended drawings is intended as a description of the presently preferred embodiment of the invention, and is not intended to represent the only form in which the present invention may be constructed or utilized. Reference throughout the detailed description to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this detailed description are not necessarily all referring to the same embodiment. The following description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments. In the following description, numerous specific details are shown to provide a thorough understanding of embodiments of the invention. One skilled in the relevant art will recognize, however, that the invention may be practiced without one or more of the specific details, or with other methods, components, materials, etc. In other instances, well-known structures, materials, or operations are not shown or described to avoid obscuring aspects of the invention. It is further understood that the use of relational terms such as first and second, and the like are used solely to distinguish one from another entity without necessarily requiring or implying any actual such relationship or order between such entities.

Referring now to FIG. 1 there is depicted an exploded perspective view of a micro electro mechanical systems (MEMS) device 10 that includes first and second septum elements 34, 36 in accordance with an aspect of the present invention. The MEMS device of the embodiment illustrated includes a generally planar substrate 12, a parylene layer 42, a device wall layer 14, a membrane layer 38 and a capping layer 40.

Referring additionally to FIG. 2A there is provided a top plan view of the MEMS device 10, as seen in a prior fabrication step (as discussed further below). It is noted that the membrane layer 38 and the capping layer 40 are not depicted for ease of illustration. FIG. 2B is a top plan view of the MEMS device 10 of FIG. 2A as finally fabricated.

In the embodiment illustrated, the device wall layer 14 includes a first septum cavity, 16, a second cavity 18, a third cavity 20 and a fourth septum cavity 22. A first channel 24 is disposed between the first septum cavity 16 and the second cavity 18. A second channel 26 is disposed between the second and third cavities 18, 20. A third channel 28 is disposed between the third cavity 20 and the fourth septum cavity 22. The first septum cavity 16 includes a first cavity entrance 30. The fourth cavity 22 includes a fourth cavity entrance 32. A first septum element 34 is disposed in the first cavity 16. In this embodiment, the first septum element 34 is partially disposed in the first channel 24. A second septum element 36 is disposed in the fourth cavity 22. In this embodiment, the first septum element 34 is partially disposed in the third channel 28. The parylene layer 42 includes first, second and third etched regions 44, 46, 48 which are aligned with the second cavity 18, the second channel 26, and the third cavity 20.

The first septum element 34 includes a first septum entry surface 56 and a first septum exit surface 58. In the embodiment illustrated, the first septum entry surface 56 is disposed adjacent the first cavity entrance 30 and the first septum exit surface 58 is disposed in the first channel 24. The second septum element 36 includes a second septum entry surface 62 and a second septum exit surface 60. In the embodiment illustrated, the second septum entry surface 62 is disposed adjacent the fourth cavity entrance 32 and the second septum exit surface 60 is disposed in the third channel 28.

The substrate 10 includes first and second electrolysis pumps 50, 52 and various leads 54 (selected ones indicated for ease of illustration) and resistors 64 (selected ones indicated for ease of illustration). It is understood that these electronic components are illustrated as merely an example, and that the invention is not restricted to any particular electronic configuration.

According to an aspect of the present invention, there is provided the MEMS device 10 includes the generally planar substrate 12, the device wall layer 14 formed upon the substrate 12, and a septum cavity (such as the first septum cavity 16) formed in the device wall layer 14. The MEMS device 10 further includes a channel (such as the first channel 24) formed in the device wall layer 14 in fluid communication with the first septum cavity 16. The MEMS device 10 further includes a septum element (such as the first septum element 34) disposed in the first septum cavity 16. The first septum element 34 is formed of a viscoelastic material. The first septum element 34 defines the first septum entry surface 56 and the first septum exit surface 58. The first septum exit surface 58 is exposed to the first channel 24 and disposed between the first septum entry surface 56 and the first channel 24. The first septum element 34 is without any openings formed through the first septum element 34 extending between the first septum entry surface 56 and the first septum exit surface 58.

Referring now to FIGS. 3A-H there are depicted cross sectional views of the MEMS device 10 as depicted along an axis 3-3 of FIG. 2B illustrating various states of fabrication. FIGS. 3A-H represent cross sectional views of the MEMS device 10 taken through a location through the first septum cavity 16. Further, referring additionally to FIGS. 4A-H there are depicted cross sectional views of the MEMS device 10 as depicted along an axis 4-4 of FIG. 2B illustrating various states of fabrication. FIGS. 4A-H represent cross sectional views of the MEMS device 10 taken through a location through the second electrolysis pump 52. The MEMS device 10 of FIG. 1 correlates to the stage of manufacture of the view of FIGS. 3H and 4H.

Figure 4A:
FIGS. 4A-H are cross sectional views of a MEMS device as depicted along an axis 4-4 of FIG. 2B illustrating various states of fabrication.

There is disclosed a method of manufacturing a micro electro mechanical systems (MEMS) device that includes an interconnect element for use with an elongate structure, such as a needle. Referring now to FIGS. 3A and 4A, the method includes the initial step of forming the substrate 12. The substrate can be any material that has a smooth surface that is compatible with MEMS processing. Typical MEMS substrate materials are silicon wafers and glass (typical glass substrates are soda lime wafers and microscope slides).

Figure 4B:
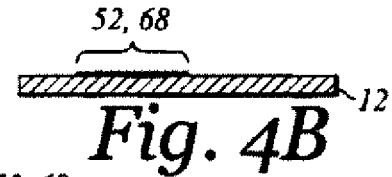

FIGS. 3A and 4A further depict an optional metal fabrication steps. These steps are performed depending upon the nature of the MEMS device that is desired. A metal layer 66 may be deposited upon the substrate 12. The metal layer 66 may take the form of copper, for example. For example, the metal layer 66 may be defined by creating a lift-off mask. Lift-off is a process similar to stenciling (put down a pattern, paint over pattern, lift-up pattern). A lift-off mask may be created by: 1) spin coating a photo-patternable material called photoresist; 2) pattern photoresist with UV light, depending on the photoresist, portions exposed to the light can be removed (positive photoresist) or portions exposed to the light remain (negative photoresist); and 3) develop photoresist to reveal pattern (substrate is accessible through unpatterned photoresist areas). Next, metal is deposited onto the photoresist mask and substrate 12. The photoresist mask is dissolved and the thickness of the metal layer 66 may be adjusted. Any metal on photoresist is lifted-off with the photoresist (such a depicted in FIG. 3B), while metal deposited on exposed portions of the substrate 12 remains (such as depicted in FIG. 4B) so as to define traces 68, such as the second electrolysis pump 52.

Figure 3C:
Figure 3D:
Figure 4C:
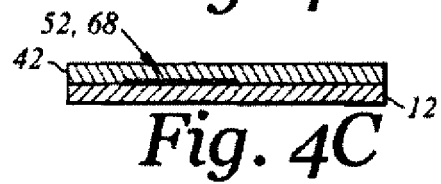
Figure 4D:
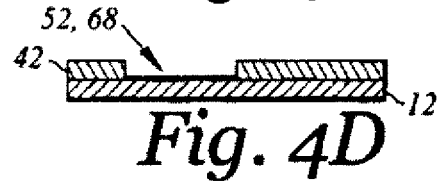

Referring to FIGS. 3C and 4C, the method may further include depositing a parylene layer 42 onto the substrate 12. Parylene has many desirable characteristics. This material is generally considered "pin-hole free"—a layer of parylene does not contain any holes that will allow fluid or gas to permeate through the layer. This material may be vapor-deposited so as to cover everything substantially uniformly and does not have to be line of sight (e.g. will cover corners and the underside of overhangs). This material is non-conductive, it provides electrical isolation of metal structures to prevent shorting. This material may be processed through etching—to form holes within parylene layers (such as by using oxygen plasma), such as to access electrode areas to connect integrated electrical components (if present). This material may undergo significant elongations (on the order of 200% elongation). This is desirable where a thermal mismatch occurs between subsequent layers (such as a rigid layer of SU-8) and the substrate 12. If MEMS device 10 is heated, the additional layer (such as SU-8) may expand more than the substrate 12, causing stress in the MEMS device 10 and the various layers that may be formed on the substrate 12. Referring to FIGS. 3D and 4D, the method may further include etching the parylene layer 42.

Figure 3E:
Figure 4E:
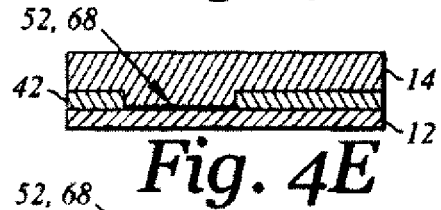

Next, the device wall layer 14 is formed. The device wall layer 14 may be formed of a rigid material. Referring to FIGS. 3E and 4E, a layer of a polymer material or plastic (such as an epoxy resin like SU-8) is spin-coated and patterned. SU-8 starts as a viscous polymer (it is a negative photoresist). This material may be spin coated to form a relative "uniform layer" of specific thickness. The layer thickness is controlled by SU-8 formula, spin speed and spin time. This material can be used to make a layer from a few microns to hundreds/thousands of microns thick (mm range). SU-8 is a negative, epoxy-type, near-UV photoresist based on EPON SU-8 epoxy resin (from Shell Chemical) that has been originally developed, and patented (U.S. Pat. No. 4,442,245 and others) by IBM. It is contemplated that this material may be formed to be relatively thick (such as 2 mm) and be relatively stable with an aspect ratio of 20 and higher. This material is characterized as having a relatively low optical absorption in the UV wavelength range. The thickness of this layer may be defined by the outer diameter of the elongate structure (such as a needle) that is to be used to pierce the septum element (as discussed below). Some sample needle sizes: 33 gauge-203 μm outer diameter; and 30 gauge-305 μm outer diameter.

Figure 3F:
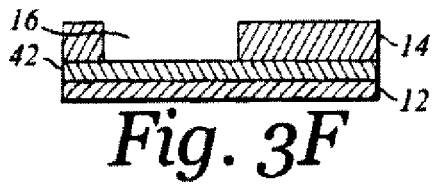
Figure 4F:
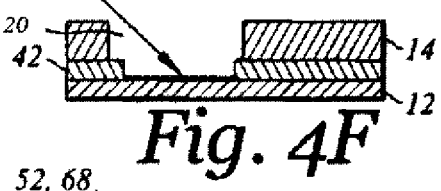
Figure 4G:
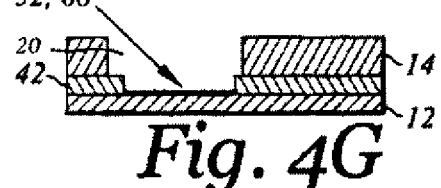

Referring to FIGS. 3F and 4F, selective portions of the device wall layer 14 may be removed. This results in the formation of the septum cavity 16 (FIG. 3F) and an adjacent first channel 24. In addition, other vacated spaces may be defined, such as the volume about electrical elements, such as the third cavity 20 (FIG. 4F).

Figure 3G:

Referring now to FIG. 3G, a polymer material such as a silicon material like polydimethylsiloxane (PDMS), is poured into the first septum cavity 16. Though not shown, this material is also poured in the second septum cavity 22. The PDMS forms to shape the first and second septum cavities 16, 22. The PDMS is allowed to cure inside first and second septum cavities 16, 22 to form the first and second septum elements 34, 36. Significantly, the PDMS material is a viscoelastic material and exhibits "self-sealing" properties. PDMS exhibits various desirable characteristics. The material starts as a viscous liquid that conforms to any shape. PDMS liquid may be made by combining base and curing agent (10:1, by weight). It is contemplated that the base and curing agent ratio may be adjusted to alter the PDMS mechanical properties. The material can be cured into a solid. The material is optically clear. It is contemplated that the first and second septum elements 34, 36 may be formed of any of those materials which are well known to one of ordinary skill in the art.

Figure 3H:
Figure 4H:
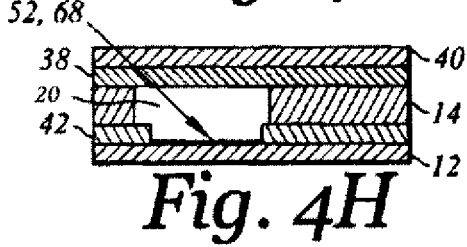

Referring to FIGS. 3H and 4H, the membrane layer 38 may be provided. This may take the form of a sheet or thin layer of PDMS to seal the device. The membrane layer 38 may be formed of half-cured PDMS which is put over the entire device. This planarizes any surface irregularities, such as of the SU-8 layer. This membrane layer 38 may be used as a capping layer. In addition, this membrane layer 38 may prevent uncured PDMS (as may be applied in later processing steps) from seeping into other locations on the device. In this regard, an uncured PDMS drop may be spread on the membrane layer 38. This may be used to "glue" glass to membrane layer 38 and to further planarize the area. The MEMS device 10 may be finally capped with the capping layer 40. A glass or silicon material may be used as the capping layer 40. This may be used to close the top of the MEMS device 10.

Next, referring to FIGS. 2A and 2B, ends of the MEMS device may be cut to expose the first septum entry surface 56 and the second septum entry surface 62 respectively of the first and second septum elements 34, 36. The first septum element 34 defines a fluid-tight seal with the device wall layer 14 at the first septum cavity 16 with respect to fluid leakage between the first channel 24 and the device wall layer 14 adjacent the septum entry surface 56. Thus, the first septum element 34 is without any openings formed through the first septum element 34 extending between the first septum entry and exit surfaces 56, 58 Likewise, the second septum element 36 is without any openings formed through the first septum element 34 extending between the first septum entry and exit surfaces 62, 60. In this regard, it is contemplated a mere washer or ring of viscoelastic material would not adequately function as either the first or second septum elements 34, 36 if fluids may readily flow through a center of the washer or ring.

According to another aspect of the present invention, there is provided a method of interacting with the micro electro mechanical systems (MEMS) device 10. The method begins with providing a MEMS device 10 such as described above. Referring now to FIG. 5A there is depicted a top plan view of the MEMS device 10 of FIG. 2B (without some features depicted for ease of illustration; namely, the membrane layer 38, the capping layer 40 and the first and second electrolysis pumps 50, 52, the leads 54 and resistors 64 are not illustrated). FIG. 6 depicts a top end perspective view of a portion the MEMS device 10 of FIG. 5a (with the membrane layer 38 and the capping layer 40). The first septum entry surface 56 is shown from this view.

Next, the method provides for piercing the septum entry surface (such as the first septum entry surface 56) with an elongate structure. Referring now to FIG. 5B there is depicted a top plan view of the MEMS device 10 of FIG. 5A as shown with a first needle 70. FIG. 7 depicts a top end perspective view of a portion of the MEMS device 10 of FIG. 5b with the first needle 70. Next, the method provides for extending the elongate structure (such as the first needle 70) through the septum exit surface (such as the first septum exit surface 58) into the first channel 24. Further, a fluid may be injected into the first channel 24 through the first needle. In this regard, FIGS. 5B and 7 depict a working fluid 72 having been injected into the second cavity 18. In this particular example, the working fluid 72 has also flowed into a portion of the first channel 24 and a portion of the second channel 26.

These figures depict how the needle 70 may pierce the first septum element 34 The needle 70 or elongate structure should be of a non-coring type so as to facilitate sealing of the displaced material formed through the first septum element 34 after removal of the needle 70 or elongate structure. In this regard, FIG. 5C depicts the MEMS device 10 after the needle 70 has been removed from the first septum element 34. Significantly, no opening persists after such removal. Significantly, because the first septum element 34 is formed of a viscoelastic material, when the first septum element 34 is pierced by an elongate structure, such as the needle 70, it is "self-sealing" when the structure is removed. Thus, a fluid-tight seal is maintained of the pierced opening after removal of the elongate structure. This allows the first septum element 34 to be reusable in nature. This is in contrast to other interconnect prior art configurations that do not allow for the removal of a delivery structure without damaging the device.

In addition, it is contemplated that the first septum element 34 is particularly useful as it provides an in-plane access to the MEMS device 10. In this regard, an elongate structure may be used that is positioned substantially parallel to the substrate 12 (such as depicted in FIG. 7). As such, this interconnect configuration does not include any structures that protract out-of-plane. This avoids problems with interference with objectives (objective lens) of a microscope when viewing the device. This also avoids having to provide supporting structures that are needed to support out of plane elements.

The elongate structure defines a longitudinal length and a structure cross-sectional area orthogonal to the longitudinal length. The first septum element 34 may extend a distance between the first septum entry surface 56 and first septum exit surface 58 parallel to the substrate 12 less than the longitudinal length. The first septum element 34 extends across an area orthogonal to the substrate greater than the structure cross-sectional area.

Referring now to FIG. 5C there is depicted a top plan view of the MEMS device 10 of FIG. 5B with a working gas 74 having been created in the MEMS device. For example, this may be a result of the electrolysis pump 50 interacting with the working fluid 72 or a chemical reaction involving the working fluid 72.

FIG. 5D is a top plan view of the MEMS device 10 of FIG. 5C as shown with a second needle 76 inserted through the second septum element 36 for removing the working gas 74 from the MEMS device 10. In this regard, it is contemplated that the first or second septum elements 34, 36 may be used to access an interior of the MEMS device 10 for adding or removing materials from within the MEMS device 10.

Referring now to FIG. 8 there is depicted a top plan view of a MEMS device 78 according to another embodiment. This view is similar to the view of FIG. 5A except of those differences noted. Like reference numerals indicate like elements. The MEMS device 78 includes a device wall layer 14 that has a first septum cavity 80, a second cavity 82, a third cavity 84 and a fourth septum cavity 86. A first septum 88 is disposed in the first septum cavity 80. The first septum 88 includes a first septum entry surface 92 and a first septum exit surface 94. A second septum 90 is disposed in the fourth septum cavity 86. The second septum 90 includes a first septum entry surface 96 and a first septum exit surface 98. In this embodiment, the cavities 80, 82, 84 and 86 have a square configuration. Likewise, the first and second septum elements 88, 90 have a square configuration. It is contemplated that while the cavities 16, 18, 20, 22 and the first and second septum elements 34, 36 have a round configuration and the cavities 80, 82, 84, 86 and the first and second septum elements 88, 90 have a square configuration, the particular configuration and cross-section may be of a variety of shapes and sizes. For example, the shapes may be of irregular shapes like a barbed configuration.

The first and second septum elements 88, 90 may provide access to the MEMS device 78 by other elongate structures other than the needle 10. For example, a sensor 100 may be introduced. Sensors may include optical devices and devices and for sensing temperature. It is contemplated that the elongate structure may be tubular and act as a catheter for providing access to other elongate elements, such as electrical conduit for electrically communicating with the interior of the device. Accordingly, the elongate structure may be of any configuration known to one of ordinary skill in the art.

What is claimed is:

1. A method of manufacturing a device for use with an elongate structure, the method comprising:
   a) forming a generally planar substrate;
   b) depositing parylene upon the substrate, and forming a device wall layer by depositing an epoxy resin upon the parylene;
   c) forming a septum cavity in the device wall layer;
   d) forming a channel formed in the device wall layer in fluid communication with the septum cavity; and
   e) forming a septum element disposed in the septum cavity, the septum element formed of a viscoelastic material, the septum element defining a septum entry surface and a septum exit surface, the septum exit surface being exposed to the channel and disposed between the septum entry surface and the channel, the septum element being without any openings formed through the septum element extending between the septum entry and exit surfaces.

2. The method of claim 1 wherein b includes:
spin coating an epoxy resin upon the parylene.

3. The method of claim 2 when b) includes;
curing the epoxy resin into a solid material.

4. The method of claim 1 wherein d) includes:
pouring a polymer in the septum cavity;
curing the polymer to form the septum element.

* * * * *